United States Patent
Moore et al.

(10) Patent No.: US 9,921,220 B2
(45) Date of Patent: *Mar. 20, 2018

(54) **PROCESS AND MATERIALS FOR THE RAPID DETECTION OF *STREPTOCOCCUS PNEUMONIAE* EMPLOYING PURIFIED ANTIGEN-SPECIFIC ANTIBODIES**

(71) Applicant: Alere Scarborough, Inc., Scarborough, ME (US)

(72) Inventors: Norman J. Moore, North Berwick, ME (US); Mary K. Konstantin, Cumberland Center, ME (US); Vladimir A. Koulchin, Portland, ME (US); Elena V. Molokova, Portland, ME (US)

(73) Assignee: Alere Scarborough, Inc., Scarborough, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/057,822

(22) Filed: Mar. 1, 2016

(65) Prior Publication Data

US 2016/0377614 A1    Dec. 29, 2016

Related U.S. Application Data

(60) Continuation of application No. 14/628,827, filed on Feb. 23, 2015, now Pat. No. 9,310,369, which is a continuation of application No. 11/982,410, filed on Oct. 31, 2007, now abandoned, which is a continuation of application No. 11/740,738, filed on Apr. 26, 2007, now abandoned, which is a continuation of application No. 10/989,050, filed on Nov. 16, 2004, now abandoned, which is a division of application No. 09/397,110, filed on Sep. 16, 1999, now Pat. No. 6,824,997, which is a continuation-in-part of application No. 09/156,486, filed on Sep. 18, 1998, now abandoned.

(51) Int. Cl.

| G01N 33/569 | (2006.01) |
|---|---|
| C07K 16/12 | (2006.01) |
| G01N 21/78 | (2006.01) |
| G01N 21/75 | (2006.01) |
| G01N 21/77 | (2006.01) |

(52) U.S. Cl.
CPC ... *G01N 33/56944* (2013.01); *C07K 16/1275* (2013.01); *G01N 21/78* (2013.01); *G01N 2021/752* (2013.01); *G01N 2021/757* (2013.01); *G01N 2021/7759* (2013.01); *G01N 2333/3156* (2013.01); *G01N 2400/10* (2013.01); *G01N 2469/10* (2013.01)

(58) Field of Classification Search
None
See application file for complete search history.

(56) References Cited

U.S. PATENT DOCUMENTS

| 4,206,094 A | 6/1980 | Yen et al. |
|---|---|---|
| 4,373,932 A | 2/1983 | Gribnau et al. |
| 4,411,832 A | 10/1983 | Cuatrecasas et al. |
| 4,514,509 A | 4/1985 | Kohler et al. |
| 4,703,017 A | 10/1987 | Campbell et al. |
| 4,751,190 A | 6/1988 | Chiapetta et al. |
| 4,780,407 A | 10/1988 | Strosberg et al. |
| 4,861,711 A | 8/1989 | Friesen et al. |
| 4,888,279 A | 12/1989 | Zeiger |
| 4,943,522 A | 7/1990 | Eisinger et al. |
| 4,954,449 A | 9/1990 | Hunter et al. |
| 5,059,591 A | 10/1991 | Janoff et al. |
| 5,098,827 A | 3/1992 | Boyle et al. |
| 5,139,933 A | 8/1992 | Green et al. |
| 5,149,622 A | 9/1992 | Brown et al. |
| 5,356,778 A | 10/1994 | Hansen et al. |
| 5,367,058 A | 11/1994 | Pitner et al. |
| 5,415,994 A | 5/1995 | Imrich et al. |
| 5,455,032 A | 10/1995 | Kenny et al. |
| 5,455,302 A | 10/1995 | Saito et al. |
| 5,536,646 A | 7/1996 | Sand et al. |
| 5,571,511 A | 11/1996 | Fischer |
| 5,602,040 A | 2/1997 | May et al. |
| 5,623,057 A | 4/1997 | Marburg et al. |
| 5,665,561 A | 9/1997 | Tuomanen et al. |
| 5,695,768 A | 12/1997 | Malcolm |

(Continued)

FOREIGN PATENT DOCUMENTS

| EP | 497524 A2 | 8/1992 |
|---|---|---|
| JP | 1032169 | 8/1977 |

(Continued)

OTHER PUBLICATIONS

"Legionnaire's Disease," (excerpt from a textbook; author anonymous) (5 pages) (1993).

AlonsoDeVelasco, et al. "*Streptococcus pneumoniae*: Virulence Factors, Pathogenesis, and Vaccines," Microbiological Reviews, 59(4): 591-603 (Dec. 1995).

Au, C.C., et al. "Evaluation of the Role of the Pneumococcal Forssman Antigen (F-Polysaccharide) in the Cross-Serotype Protection Induced by Pneumococcal Subcellular Preparations," 31(1): 169-173 (Jan. 1981).

Author Anonymous, "Bacterial Pneumonia Part I. Issues on Prevention of Nosocomial Pneumonia, 1994,"—Excerpt from CDC On-Line Guidelines (15 pages entitled "Bacterial Pneumonia").

Bangsborg, J. M., et al.; "Cross-reactive *Legionella* antigens and the antibody response during infection," APMIS 99:854-865 (Apr. 2, 1991).

Barthe et al., "Common Epitope on the Lipopolysaccharide of *Legionella pneumophila* Recognized by a Monoclonal Antibody," Journal of Clinical Microbiology, 26(5):1016-1023 (1988).

(Continued)

*Primary Examiner* — Mary Lyons
(74) *Attorney, Agent, or Firm* — Foley Hoag LLP

(57) ABSTRACT

Disclosed is a cell wall C-polysaccharide antigen of *Streptococcus pneumoniae* which contains not more than 10% by weight of protein, and preferably less which has been purified with 0.1N Na OH prior to deproteinizing. Also disclosed are polyvalent antibodies raised against *Streptococcus pneumoniae* which have been affinity purified by passing them over a chromatographic affinity matrix to which is coupled the purified and at least partially deproteinized antigen to render them antigen-specific.

12 Claims, 1 Drawing Sheet

(56) References Cited

U.S. PATENT DOCUMENTS

| | | | |
|---|---|---|---|
| 5,770,208 A | 6/1998 | Fattom et al. | |
| 5,773,007 A | 6/1998 | Penney et al. | |
| 5,798,273 A | 8/1998 | Shuler et al. | |
| 5,807,715 A | 9/1998 | Morrison et al. | |
| 5,847,112 A | 12/1998 | Kniskern et al. | |
| 5,866,140 A | 2/1999 | Fattom et al. | |
| 5,871,951 A | 2/1999 | Weiser | |
| 5,879,881 A | 3/1999 | Rubenstein | |
| 5,948,900 A | 9/1999 | Yother et al. | |
| 5,978,273 A | 11/1999 | Shigemura | |
| 5,989,542 A | 11/1999 | Pier et al. | |
| 6,010,910 A | 1/2000 | Radcliffe et al. | |
| 6,057,421 A | 5/2000 | Muller et al. | |
| 6,168,796 B1 | 1/2001 | Malcolm | |
| 6,194,221 B1 | 2/2001 | Rehg et al. | |
| 6,217,866 B1 | 4/2001 | Schlessinger et al. | |
| 6,245,335 B1 | 6/2001 | Masure et al. | |
| RE37,437 E | 11/2001 | Friesen et al. | |
| 6,495,139 B2 | 12/2002 | Tuomanen et al. | |
| 6,566,500 B1 | 5/2003 | Vitetta et al. | |
| 6,610,293 B1 | 8/2003 | Fischer et al. | |
| 6,824,997 B1 * | 11/2004 | Moore | C07K 16/1275 422/423 |
| 6,979,576 B1 | 12/2005 | Cheng et al. | |
| 7,169,903 B2 | 1/2007 | Schuman et al. | |
| 7,635,483 B2 | 12/2009 | Cleary et al. | |
| 7,718,375 B2 | 5/2010 | Piasio et al. | |
| 8,252,546 B2 | 8/2012 | Briles et al. | |
| 8,313,955 B2 | 11/2012 | Wu et al. | |
| 9,310,369 B2 * | 4/2016 | Moore | C07K 16/1275 |
| 2002/0015693 A1 | 2/2002 | Metzger et al. | |
| 2003/0157115 A1 | 8/2003 | Bay et al. | |
| 2004/0247605 A1 | 12/2004 | Kokai-Kun et al. | |
| 2006/0121058 A1 | 6/2006 | Malley et al. | |
| 2007/0265433 A1 | 11/2007 | Moore et al. | |
| 2009/0186368 A1 | 7/2009 | Raven et al. | |
| 2010/0227341 A1 | 9/2010 | Briles et al. | |
| 2015/0202309 A1 | 7/2015 | Emini et al. | |
| 2015/0219648 A1 | 8/2015 | Moore et al. | |

FOREIGN PATENT DOCUMENTS

| | | |
|---|---|---|
| JP | 1503174 | 6/1981 |
| JP | 3176659 | 7/1991 |
| JP | H6508215 A | 9/1994 |
| JP | 2001502046 | 2/2001 |
| WO | WO-88/08534 A1 | 11/1988 |
| WO | WO-9210936 A1 | 7/1992 |
| WO | WO-92/21977 A1 | 12/1992 |
| WO | WO-9400149 A1 | 1/1994 |
| WO | WO-9412641 A1 | 6/1994 |
| WO | WO-96/28008 | 9/1996 |
| WO | WO-00/16803 | 3/2000 |
| WO | WO-2009/122714 A1 | 10/2009 |

OTHER PUBLICATIONS

Bennett, Larry G., et al.; "Binding studies with antibodies having phosphorylcholine specificity and fragments derived from their homologous *Streptococcus pneumoniae* type 27 capsular polysaccharide," Journal of Immunology 122(6):2356-2362 (Jun. 1979).

Benzing, et al. Specific Capsular Polysaccharide of Type 46 *Streptococcus pneumoniae* (American Type 73), Infection and Immunity, 32(3): 1024-1027 (Jun. 1981).

Berdal et al.,"Detection of *Legionella pneumophila* Antigen in Urine by Enzyme-Linked Immunospecific Assay," Journal of Clinical Microbiology, 9(6):575-578 (1979).

Bibb et al., "Detection of Soluble *Legionella pneumophila* Antigens in Serum and Urine Specimens by Enzyme-Linked Immunosorbent Assay with Monoclonal and Polyclonal Antibodies," Journal of Clinical Microbiology, 20(3):478-482 (1984).

Binax Legionella Urinary Antigen EIA, Product Instructions.

Binax NOW Legionella Urinary Antigen Test, Product Instructions.

Bosshardt, Stephen C., et al.; "Flagella are a positive predictor for virulence in *Legionella*," Microbial Pathogenesis 23:107-112 (1997).

Bromberg, K, et al.; "Pneumococcal C and type polysaccharide detection in the concentrated urine of patients with bacteremia," Med Microbiol Immunol 179:335-338 (1990).

Brundish, et al. "Pneumococcal C-Substance, a Ribitol Teichoic Acid Containing Choline Phosphate," Biochemical Journal, 110: 573-582 (1968).

Brundish, et al.; "The Characterization of Pneumococcal C-Polysaccharide as a Ribitol Teichoic Acid," Biochem. J. 105:30c-31c (1967).

Canadian Office Action for 2,427,693 dated Jul. 4, 2011.

Canadian Office Action for 2,427,693 dated May 23, 2013.

Carratala et al., "Risk Factors for Nosocomial *Legionella pneumophila* Pneumonia," Am. J. Respir. Crit. Care Med., 149:625-629 (1994).

Chinese Office Action for Application No. 200510084709.5 dated Jul. 31, 2009.

Chinese Office Action for Application No. 200520084709.5 dated Jan. 5, 2007.

Chu, C, et al.; "Further Studies on the Immunogenicity of *Haemophilus influenzae* Type b and Pneumococcal Type 6A Polysaccharide-Protein Conjugates," Infection and Immunity 40(1):245-256 (Apr. 1983).

Ciesielski et al., "Serogroup Specificity of *Legionella pneumophila* Is Related to Lipopolysaccharide Characteristics," Infection and Immunity, 51(2):397-404 (1986), Clinical Microbiology, 25(1):29-33 (1998).

Coligan, John, E., et al. "A Disaccharide Hapten From Streptococcal Group C Carbohydrate That Cross-Reacts With the Forssman Glycolipid," The Journal of Immunology, 118(1): 6-11 (Jan. 1977.).

Dominguez et al., "Comparison of the Binax *Legionella* Urinary Antigen Enzyme Immunoassay (EIA) with the Biotest *Legionella* Urin Antigen EIA for Detection of *Legionella* Antigen in both Concentrated and Nonconcentrated Urine Samples," Journal of Clinical Microbiology, 36(9):2718-2722 (1998).

Dowson et al., "Penicillin-resistant viridans streptococci have obtained altered pencillin-binding protein genes from penicillin-resistant strains of *Streptococcus pneumoniae*," Proc Natl Acad Sci USA, 87: 5858-5862 (Aug. 1990), Microbiology.

Edelstein, P.H., "Laboratory Diagnosis of Legionnaires Disease: an Update from 1984," State of the Art Lecture; journal unknown (1993).

Edelstein, P.H., "State-of-the-Art Clinical Article," Clinical Infectious Diseases, 16:741-749 (1993).

Examiner's Decision of Rejection dated Jan. 13, 2015, from JP 2011-151090.

Fischer et al. "Teichoic acid and lipoteichoic acid of *Streptococcus pneumoniae* possess identical chain structures. A reinvestigation of teichoid acid (C polysaccharide)," European Journal of Biochemistry, 215(3): 851-857 (1993).

Flesher et al., "Isolation of a Serogroup 1-Specific Antigen from *Legionella pneumophila*," The Journal of Infectious Diseases, 145(2):224-233 (1982).

Fraser et al., "Legionnaires' Disease," The New England Journal of Medicine, 297(22):1189-1197 (1977).

Gillespie, SH et al, "Diagnosis of *Streptococcus pneumoniae* by quantitative enzyme linked immunosorbent assay of C-polysaccharide antigen," J. Clinical Pathology, 47:749-751 (Aug. 1994).

Gillespie, SH et al., "Detection of C-polysaccharide in serum of patients with *Streptococcus pneumoniae* bacteraemia," J. Clin. Pathol. 48:803-806 (1995).

Gillespie, SH, "The diagnosis of *Streptococcus pneumoniae* infections," Reviews in Medical Microbiology 5(4):224-232 (1994).

Gotschlich, Emily C. et al., "Structural and Immunological Studies on the Pneumococcal C Polysaccharide," The Journal of Biological Chemistry 242(3):463-470 (Feb. 10, 1967).

Guillet et al., "Characterization, Serological Specificity, and Diagnostic Possibilities of Monoclonal Antibodies Against *Legionella pneumophila*," Journal of Clinical Microbiology, 18(4):793-797 (1983).

(56) References Cited

OTHER PUBLICATIONS

Hackman et al., "Comparison of Binax Legionella Urinary Antigen EIA Kit with Binax RIA Urinary Antigen Kit for Detection of *Legionella pneumophila* Serogroup 1 Antigen," Journal of Clinical Microbiology, 34(6):1579-1580 (1996).
Havas, H. Francis, et al.; "Effect of TEPC-183 Plasmacytoma on Resistance of Passively or Actively Immunized BALB/c Mice to Infection with *Streptococcus pneumoniae*," Cancer Research 44:3299-3302 (Aug. 1984).
Helbig et al., "Antigenic Lipopolysacchararide Components of *Legionella pneumophila* Recognized by Monoclonal Antibodies: Possibilities and Limitations for Division of the Species into Serogroups," Journal of Clinical Microbiology, 35(11):2841-2845 (1997).
Helbig et al., "Diagnostik von Legionella-Pneumonien durch Nachweis der Antigenurie mittels Enzymimmunoassay unter Verwendung von 6 unterschiedlichen Antikorperspezifitaten," Z. Gesamte Hug. 35:591-593 (1989) [in German with English Abstract].
Heymann, H., et al., "Structure of Streptococcal Cell Walls," The Journal of Biological Chemistry 238(2):502-509 (Feb. 1963).
Hogg, Stephen D., et al. "Occurrence of Lipoteichoic Acid in Oral Streptococci," Int'l Journal of Systematic Bacteriology, 47(1): 62-66 (Jan. 1997).
Holmberg, H et al, "Detection of C Polysaccharide in *Streptococcus pneumoniae* in the Sputa of Pneumonia Patients by an Enzyme-Linked Immunosorbent Assay," J. Clinical Microbiology 22(1):111-115 (Jul. 1985).
Horwitz et al., "Prospects for Vaccine Development," Presented at 4th International Symposium on Legionella, In Barbaree, J.M., Breiman, R.F. & DuPour, A.P. (Eds.) *Legionella*, 2 pages (1993).
Japanese Office Action for Application No. 2000-565904 dated Jul. 28, 2009.
Japanese Office Action for Application No. 2001-563134 dated Aug. 17, 2010.
Japanese Office Action for Application No. 2001-563134 dated Mar. 15, 2011.
Japanese Patent Application No. 2000-573764 Office Action dated Mar. 8, 2011.
Jikkenhou, Seibutsukagaku 20; Methods for isolation, Purification of Polysaccharides, Experimental Methods in Biochemistry, Gakkai Syuppnan Center, 1087, pp. 19-35. (1987).
Jurgens et al., "Cross-Reacting Lipopolysaccharide Antigens in *Legionella pneumophila* Serogroups 1 to 14," Infection and Immunity, 63(6):2180-2184 (1995).
Jurgens, D. et al., "Identification of Legionella Species by Lipopolysaccharide Antigen Pattern," J. Clin. Microbiol., 35(12):3054-3057 (1997).
Kasahara, Y., et al., "Simple devices and their possible application in clinical laboratory downsizing," Clinica Chimica Acta 267(1):87-102 (1997).
Kazandjian et al., "Rapid Diagnosis of *Legionella pneumophila* Serogroup 1 Infection with the Binax Enzyme Immunoassay Urinary Antigen Test," Journal of Clinical Microbiology, 35(4):954-956 (1997).
Keller et al., "Community Outbreak of Legionnaires' Disease: An Investigation Confirming the Potential for Cooling Towers to Transmit *Legionella* Species," Clinical Infectious Diseases, 22:257-261 (1996).
Klein, Roger A., et al. "The aqueous solution structure of the tetrasaccharide-ribitol repeat-unit from the lipoteichoic acid of *Streptococcus pneumoniae* strain R6 determined using a combination of NMR spectroscopy and computer calculations," 256: 189-222 (1994).
Knirel et al., "The structure of the O-specific chain of Legionella pneumophila serogroup 1 lipopolysaccharide," Eur. J. Biochem., 221(1):239-245 (1994).
Kohler et al., "Antigen Detection for the Rapid Diagnosis of Mycoplasma and Legionella Pneumonia," Diagnosis Microbiol. Infect. Disease, 4:47S-59S (1986).
Kohler et al., "Onset and Duration of Urinary Antigen Excretion in Legionnaires Disease," Journal of Clinical Microbiology, 20(4):605-607 (1984).
Kohler et al., "Rapid Radioimmunoassay Diagnosis of Legionnaires' Disease," Annals of Internal Medicine, 94(5):601-605 (1981).
Kolkman, et al. "Carbohydrates, Lipids, and Other Natural Products: Functional Analysis of Glycosyltransferases Encoded by the Capsular Polysaccharide Biosynthesis Locus of *Streptococcus pneumniae* Serotype 14," The Journal of Biological Chemistry, 272(31): 19502-19508 (1997).
Koskela, M., et al., "Enzyme Immunoassay for Detection of Immunoglobulin G (IgG), IgM, and IgA Antibodies against Type 6B Pneumococcal Capsular Polysaccharide and Cell Wall C Polysaccharide in Chinchilla Serum," Journal of Clinical Microbiology 30(6):1485-1490 (Jun. 1992).
Kouza, Shin-Seikagaku Jikken, Protein I "Isolation, Purification, Nature," (Modern Experimental Biochemistry), pp. 214-216 (1990).
Kovacs, et al. "A Functional dlt Operon, Encoding Proteins Required for Incorporation of D-Alanine in Teichoic Acides in Gram-Positive Bacteria, Confers Resistance to Cationic Antimicrobial Peptides in *Streptococcus pneumoniae*," Journal of Bacteriology, 188(16): 5797-5805 (Aug. 2006).
Krook, Aud et al, "Pneumococcal Antigens in Sputa: ELISA for the Detection of Pneumococcal C-Polysaccharide in Sputa from Pneumonia Patients," Diagn. Microbiol. Infect. Dis. 7:73-75 (1987).
Laferriere, CA et al, "The synthesis of *Streptococcus pneumoniae* polysaccharide-tetanus toxoid conjugates and the effect of chain length on immunogenicity," Vaccine 15(2):179-186 (Feb. 1997).
Leibl et al., "Separation of polysaccharide-specific human immunoglobulin G subclasses using a Protein A Superose column with a pH gradient elution system," Journal of Chromatography, 639:51-56 (1993).
Leland et al., "Evaluation of the L-CLONE *Legionella pneumophila* Serogroup I Urine Antigen Latex Test," Journal of Clinical Microbiology, 29(10):2220-2223 (1991).
Liu, TY, et al., "The Chemical Composition of Pneumococcal C-Polysaccharide," The Journal of Biological Chemistry 238(6):1928-1934 (Jun. 1963).
Mangiafico et al., "Rapid and Sensitive Method for Quantitation of *Legionella pneumophila* Serogroup I Antigen from Human Urine," Journal of Clinical Microbiology, 13(5):843-845 (1981).
Manjula, B.N. et al; "Affinity of horse anti-phophorylcholine antibodies for some pneumococcal polysaccharides, contribution of the polysaccharide backbone"; Immunochemistry, 15: 269-271 (1978).
Manning, James. M. "Chemistry and Metabolism of Macromolecules: Chromatographic Determination of the d- and l-Amino Acid Residues in Pneumococcal C-Polysaccharide," Journal of Biological Chemistry, 246:(9): 2926-2929 (May 10, 1971).
Marston et al, "Surveillance for Legionnaires' Disease," Arch. Intern. Med., 154:2417-2422 (1994).
Moore et al., "Development of an Immunochromatographic (ICT) Assay for Identification of Legionella Pneumophila," Abstract C4-33, American Society for Microbiology Meeting, May 17-21, 1998.
Moore et al., "Development of Immunosorbent (ELISA) and Immunochromatographic (ICT) Assays for the Detection of Food-Borne Pathogen *E. coli* 0157:H7," Abstract, Poster presented at American Society or Microbiology Meeting, New Orleans (1996).
More et al., "Development of an Immunochromatographic (ICT) Assay for the Detection of Legionella Pneumophila," Abstract, Gen. Meet. Am. Soc. Microbiol., p. 203; (1998).
Murdoch et al., "Use of the Polymerase Chain Reaction to Detect *Legionella* DNA in Urine and Serum Samples from Patients with Pneumonia," Clinical Infectious Diseases, 23:475-480 (1996).
Nagel, et al. "Teichoic Acids in Pathogenic *Staphylococcus aureus*," Journal of Clinical Microbiology, 6(3): 233-237 (Sep. 1977).
Nolte et al., "Electrophoretic and Serological Characterization of the Lipopolysaccharides of *Legionella pneumophila*," Infection and Immunity, 52(3):676-681 (1986).
Nowinski, et al. "Human Monoclonal Antibody Against Forssman Antigen," Science, 210: 537-539 (Oct. 31, 1980).
Office Action for U.S. Appl. No. 11/982,410 dated Aug. 30, 2013.

(56) References Cited

OTHER PUBLICATIONS

Office Action for U.S. Appl. No. 11/982,410 dated Feb. 14, 2014.
Office Action for Japanese Application No. 2011-031137 dated Oct. 30, 2012.
Office Action in U.S. Appl. No. 11/761,255 dated Jun. 18, 2013.
Office Action in U.S. Appl. No. 11/761,255 dated Dec. 23, 2010.
Office Action in U.S. Appl. No. 11/982,400 dated Jun. 20, 2013.
Office Action in U.S. Appl. No. 11/982,410 dated Apr. 10, 2013.
Office Action in U.S. Appl. No. 11/982,410 dated Jan. 31, 2012.
Office Action in U.S. Appl. No. 11/982,410 dated Sep. 26, 2012.
Otten et al., "Serospecific Antigens of Legionella pneumophila," Journal of Bacteriology, 167(3):893-904 (1986).
Parkinson, Alan J., et al., "Quantitation of Pneumococcal C Polysaccharide in Sputum Samples from Patients with Presumptive Pneumococcal Pneumonia by Enzyme Immunoassay," Journal of Clinical Microbiology 30(2):318-322 (Feb. 1992).
Pavlova et al., "Non-Instrumental Immunoassay Based on Coloured Polyacrolein Latex: Application to Group-Specific Polysaccharide of Streptococcus pyogenes," Article, Bioorganisches Kaya Khimiya, 20(7):731-739 (1994) (in Russian language with English abstract on p. 739).
Pavlova et al., "Non-Instrumental immunoassay based on coloured polyacrolein latex: application to group-specific polysaccharide of Streptococcus pyogenes," J. Immunoassay, 16(2):199-212 (1995).
Petitjean, F. et al., "Isolation, Purification and partial Analysis of the Lipopolysaccharide Antigenic Determinant Recognized by a Monocolonal Antibody to Legionella Pneumophila Serogroup 1," Res. Microbiol., 141(9):1077-1094 (1990).
Plouffe et al., "Reevaluation of the Definition of Legionnaires' Disease: Use of the Urinary Antigen Assay," Clinical Infectious Diseases, 20:1286-1291 (1995).
Poxton, Ian R., et al., "The Structure of C-Polysaccharide from the Walls of Streptococcus pneumoniae," Biochem. J. 175:1033-1042 (1978).
Ramirez et al., "Rapid Tests for the Diagnosis of Legionella Infections," KMA Journal, 92:62-65 (1994).
Reingold et al., "Legionella Pneumonia in the United States: The Distributin of Serogroups and Species Causing Human Illness," The Journal of Infectious Disease, 149(5):819 (1984).
Roig et al., "Comparative Study of Legionella pneumophila and Other Nosocomial-Acquired Pneumonias," Chest, 99:344-350 (1991).
Rosen, IA et al, "Antibodies to pneumococcal polysaccharides in human milk: lack of relationship to colonization and acute otitis media," Pediatr Infect Dis J. 15(6):498-507 (Jun. 1996).
Ruf et al., "Prevalence and Diagnosis of Legionella Pneumonia: A 3-Year Prospective Study with Emphasis on Application of Urinary Antigen Detection," Journal of Infectious Disease, 162:1341-1348 (1989).
Sathapatayavongs et al., "Rapid Diagnosis of Legionnaires' Disease by Urinary Antigen Detection," the American Journal of Medicine, 72:576-582 (1982).
Schwab, John H., et al., "Immunological Studies on a C polysaccharide Complex of Group A Streptococci Having a Direct Toxic Effect on Connective Tissue," J. of Experimental Medicine, pp. 295-307 (1959).
Sippel, JE et al, "Detection of Neisseria meningitidis Group A, Haemophilus influenzae Type b, and Streptococcus pneumoniae Antigens in Cerebrospinal Fluid Specimens by Antigen Capture Enzyme-Linked Immunosorbent Assays," J. Clin. Microbiology 20(2):259-265 (Aug. 1984).
Sjogren, AM et al, "Etoilogic Diagnosis of Pneumonia by Antigen Detection: Crossreactions Between Pneumococcal C-Polysaccharide and Oral Microorganisms," Diagnostic Microbiology and Infectious Disease 6(3):239-248 (Mar. 1987).
Sjogren, AnnMargaret, et al. "Deomonstration of Cross-reactions Between Pneumococci and α-Streptococci Using Gold-labelled Mono- and Polyclonal Antibodies and Elctron Microscopy," Diagn. Microbiol. Infect. Dis., 10: 7-21 (1988).
Sjogren, et al.; "A highly specific two-site ELISA for pneumococcal C-polysaccharide using monoclonal and affinity-purified polyclonal antibodies," J Immunol Methods 102(1):93-100 (Aug. 24, 1987).
Skerra, A, et al., "Assembly of a Functional Immunoglobulin FV Fragment in Escherichia coli," Science 240:1038-1041 (May 20, 1988).
Skov Sorensen, "Monoclonal Phosphorylcholine Antibody Binds to Beta-Lipoprotein from Different Animal Species," Infection and Immunity 53(2): 264-266 (Aug. 1986).
Skov Sorensen, et al., "Cross-Reactions between Pneumococci and Other Streptococci Due to C Polysaccharide and F Antigen," Journal of Clinical Microbiology 25(10):1854-1859 (Oct. 1987).
Skov Sorensen, et al., "Ultrastructural Localization of Capsules, Cell Wall Polysaccharide, Cell Wall Proteins, and F Antigen in Pneumococci," Infection and Immunity 56(8):1890-1896 (1988).
Skov Sorensen, U. B., et al. "Covalent linkage between the capsular polysaccharide and the cell wall peptidoglycan of Streptococcus pneumoniae revealed by immunochemical methods," Microbial Pathogenesis 8: 325-334 (1990).
Stout et al., "Legionellosis," The New England Journal of Medicine, 337:682-687 (1997).
Stout et al., "Potable Water as a Cause of Sporadic Cases of Community-Acquired Legionnaires' Disease," New England Journal of Medicine, 326:151-155 (1992).
Stroop, Corne J.M., et al., "Structural analysis and chemical depolymerization of the capsular polysaccharide of Streptococcus pneumoniae type 1," Carbohydrate Research, 337: 335-344 (2002).
Stuertz, K et al, "Enzyme Immunoassay Detecting Teichoic and Lipoteichoic Acids versus Cerebrospinal Fluid Culture and Latex Agglutination for Diagnosis of Streptococcus pneumoniae Meningitis," J. Clinical Microbiology 36(8):2346-2348 (Aug. 1998).
Sundberg-Kovamees, M., et al., "Interaction of the C-polysaccharide of Streptococcus pneumoniae with the receptor asialo-GM1," Microbial Pathogenesis 21:223-234 (1996).
Szu, S.C., et al, "Protection Against Pneumococcal Infection in Mice Conferred by Phosphocholine-Binding Antibodies: Specificity of the Phosphocholine Binding and Relation to Several Types," Infection and Immunity 39(2):993-999 (Feb. 1983).
Szu, S.C., et al., "Rabbit antibodies to the cell wall polysaccharide of Streptococcus pneumoniae fail to protect mice from lethal challenge with encapsulated pneumococci," Infection and Immunity 54(2):448-455 (Nov. 1986).
Ta et al., "Comparison of Culture Methods for Monitoring Legionella Species in Hospital Potable Water Systems and Recommendations for Standardization of Such Methods," Journal of Clinical Microbiology, 33(8):2118-2123 (1995).
Tang et al., "Broad-Spectrum Enzyme-Linked Immunosorbent Assay for Detection of Legionella Soluble Antigens," Journal of Clinical Microbiology, 24(4):556-558 (1986).
Tang et al., "Detection of Legionella Antigenuria by Reverse Passive Agglutination," Journal of Clinical Microbiology, 15(6):998-1000 (1982).
Tang et al., "Legionella Antigenuria: Six-Year Study of Broad-Spectrum Enzyme-Linked Immunosorbent Assay as a Routine Diagnostic Test," (Journal Unknown), 12-13 (1986).
Thacker et al., "Comparison of Slide Agglutination Test and Direct Immunofluorescence Assay for Identification of Legionella Isolates," Journal of Clinical Microbiology, 18(5):1113-1118 (1983).
Tilton et al., "Legionnaires' Disease Antigen Detected by Enzyme-Linked Immunosorbent Assay," Annals of Internal Medicine, 90:697-698 (1979).
Waltman, II, W.D., et al. "Cross-Reactive Monoclonal Antibodies for Diagnosis of Pneumococcal Meningitis," Journal of Clinical Microbiology, 26(9): 1635-1640 (Sep. 1988).
Weiner et al., "Immunodiagnosis of systemic aspergillosis. I. Antigenemia detected by radioimmunoassay in experiemental infection," J. Lab. Clin. Med., Abstract, 93:111-119 (1979).
Westphal, O. et al, "Bacterial Lipopolysaccharides," Method Carbohydrate Chemistry vol. 5, pp. 83-91 (1965).
Wetherall, B., et al.; "Enzyme-Linked Immunosorbent Assay for Detection of Haemophilus influenzae Type b Antigen," J Clin Microbiol 11(6):573-580 (Jun. 1980).

(56) References Cited

OTHER PUBLICATIONS

Yang, et al. "Comparative Structural and Molecular Characterization of *Streptococcus pneumoniae* Capsular Polysaccharide Serotype 10*," Journal of Biological Chemistry, 286(41): 35813-35822 (Oct. 14, 2011).

Yolken, RH et al., "Enzyme Immunoassay for Detection of Pneumococcal Antigen in Cerebrospinal Fluid," J. of Clinical Microbiology 20(4):802-805 (Oct. 1984).

Yother, J., et al., "Protection of Mice from Infection with *Streptococcus pneumoniae* by Anti-Phosphocholine Antibody Infection and Immunity," 36(1): 184-188 (Apr. 1982).

Yother, Janet, et al. "Generation and Properties of a *Streptococcus pneumoniae* Mutant Which Does Not Require Choline or Analogs for Growth," 180(8): 2093-2101 (1998).

\* cited by examiner

PROCESS AND MATERIALS FOR THE RAPID DETECTION OF *STREPTOCOCCUS PNEUMONIAE* EMPLOYING PURIFIED ANTIGEN-SPECIFIC ANTIBODIES

PARENT APPLICATION

This application is a continuation of U.S. application Ser. No. 14/628,827, filed Oct. 31, 2007, now U.S. Pat. No. 9,310,369, which is a continuation of U.S. application Ser. No. 11/982,410, filed Oct. 31, 2007, now abandoned, which is a continuation of U.S. application Ser. No. 11/740,738, filed Apr. 26, 2007, now abandoned, which is a continuation of U.S. application Ser. No. 10/989,050, filed Nov. 16, 2004, now abandoned, which is a division of U.S. application Ser. No. 09/397,110 filed Sep. 16, 1999, now U.S. Pat. No. 6,824,997, which is in turn a continuation in part of U.S. application Ser. No. 09/156,486, filed Sep. 18, 1998, now abandoned, in the names of the same inventors, the contents of which are incorporated herein by reference in their entireties.

BRIEF DESCRIPTION OF THE INVENTION

The present invention relates to a purified carbohydrate antigen of *S. pneumoniae* and its use in affinity purifying antibodies raised in an animal against *S. pneumoniae* bacteria or against the carbohydrate antigen. The affinity purified antibodies are especially useful in a specific and sensitive immunochromatographic ("ICT") assay, performable within about 15 minutes, for the detection of *Streptococcus pneumoniae* in a bodily fluid, such as urine or cerebrospinal fluid, of a patient showing clinical signs of an infection caused by *S. pneumoniae*.

BACKGROUND OF THE INVENTION

*Streptococcus pneumoniae* ("*S. pneumoniae*") is a leading causative organism of pneumonia-type illnesses and other lower respiratory tract infections such as bronchitis, as well as of upper respiratory tract infections, including infectious otitis media and sinusitis and of disseminated invasive infections, including bacteremia and meningitis. When not properly diagnosed and treated, *S. pneumoniae* pneumonic infection may lead to any of pericarditis, empyema, purpura fulminans, endocarditis or at least one type of arthritis, where *S. pneumoniae* is the causative organism in each instance. Such pneumonic infection is also often a precursor of bacteremia or meningitis. To now, it nevertheless is common for pneumonia arising from *S. pneumoniae* to be diagnosed and treated somewhat empirically.

To a significant extent, this is because the tests presently available for the detection of *S. pneumoniae* are either (1) time consuming, labor intensive and in need of instrumental assistance for reading results, or (2) lacking in sensitivity and/or specificity. Because of problems associated with lack of sensitivity and/or specificity, e.g., physicians tend toward conservatively prescribing expensive, broad spectrum antibiotics for patients with pneumonia-type respiratory infections in lieu of prescribing a less expensive antibiotic specific to *S. pneumoniae* where it would adequately cure the infection. This and other liberal prescribing of broad spectrum antibiotics is, of course, a major cause of today's well-publicized medical crisis consequent from the increasing resistance of many types of infectious bacteria to previously highly efficacious antibiotics. This crisis and the potential untoward consequences for at least some patients of empirical diagnosis and treatment are among many reasons why a reliable and rapid assay for detecting *S. pneumoniae* in human body fluids is needed.

Pneumonia caused by *S. pneumoniae* is a serious disease, estimated to occur at the rate of one to five cases per 1,000 persons per year in the United States alone. Depending upon the age and state of health (based on unrelated factors) of patients infected with *S. pneumoniae*-caused pneumonia, the disease has a mortality rate of between 4 percent and 30 percent of infected patients.

The most time-honored methods of attempting to diagnose *S. pneumoniae*-caused diseases, and especially pneumonia, involve the Gram stain and culture of expectorated sputum of patients suspected of harboring the disease, followed by biochemical identification methods. This procedure requires in the order of one to four days from start to finish. It has proved to be an unsatisfactory diagnostic tool because (1) other bacteria present in the patient's saliva often overgrow the sputum culture, and (2) *S. pneumoniae* frequently is present in the human upper respiratory tract even when no sign of disease attributable to this bacterium is present in the individual. For example, it is estimated that some 30 percent of U.S. children are habitual carriers of *S. pneumoniae*. Adults, too may become colonized by *S. pneumoniae* without themselves entering a disease state. The carriage rates of the organism by both children and adults increase with crowding conditions and during winter months.

Co-agglutination, latex particle agglutination and counter-immunoelectrophoresis methods for detecting the polysaccharide capsular antigens of *S. pneumoniae* in sputum specimens have been developed and are rapid, but they have not been shown to exhibit reliable sensitivity or specificity, probably because there are some 83 serotypes of *S. pneumoniae*, each of which may vary in immunogenicity and in other respects. The commercial polyvalent antiserum developed and used for these tests contains antibodies to all 83 of the *S. pneumoniae* serotype antigens, but it nevertheless may fail to detect the less immunogenic antigen serotypes. This polyvalent antiserum also has shown cross-reactivity with other streptococci and some other infectious bacteria, e.g., *Haemophilus influenzae*. Hence both false-negative and false-positive reactions may occur randomly when these tests are used on sputum samples.

Several enzyme-immunoassays ("EIA") have been developed which are based on detection of the pneumococcal C-polysaccharide antigen that has been found to be present in the pneumococcal cell wall of all of the *S. pneumoniae* serotypes. See, e.g., Parkinson, A. J., Rabiego, M. E., Sepulveda, C., Davidson, M. and Johnson, C., 30 *J. Clin. Microbiol.* 318-322 (1992). This C-polysaccharide antigen is a phosphocholine-containing polysaccharide derived from teichoic acid. These EIA assays are of acceptable specificity and sensitivity even though most often performed on sputum samples. Each such assay, however, requires two to three hours performance time after sample collection as well as the use of instrumentation normally available primarily in clinical laboratories. In addition, these assays need to be run by, or under close supervision of, trained personnel.

Reliance upon sputum samples to diagnose *S. pneumoniae* infections is frequently less than satisfactory in achieving a diagnosis of *S. pneumoniae*-caused pneumonia, and not just because of the potential for contamination of the sample by other bacteria in the mouth and/or by indigenous upper respiratory tract *S. pneumoniae*. Sputum is often difficult to collect; moreover, once medication of the patient is commenced, the number of viable *S. pneumoniae* in sputum rapidly decreases. In particular, the presence of the C-polysaccharide antigen in sputum may rapidly become difficult to detect if an antibiotic therapy is used that attacks the cell wall of the *S. pneumoniae* microorganism. When *S. pneumoniae* causes infectious otitis media, meningitis and various other aforementioned infectious disease states, sputum samples are of no aid in diagnosis.

Collection of blood cultures from patients suspected of *S. pneumoniae* infection eliminates the contamination problems that attend sputum samples. Where blood serum samples are found to contain *S. pneumoniae*, diagnosis of various diseases of which it is causative may readily be made. The drawback here is that only about 20 percent of all pneumonia patients infected by *S. pneumoniae* become bacteremic; therefore, relying solely on blood samples to diagnose *S. pneumoniae*-caused pneumonia may yield false-negative results.

Urine samples have been found to be the most reliable and convenient ones to use in detecting *S. pneumoniae*-caused pneumonia because they can be non-invasively obtained; they will not be contaminated with oral microflora; and the presence of the bacterium in urine persists, albeit at a constantly decreasing level of concentration, even after patient therapy has been initiated, so that daily monitoring of patient urine samples to assess the efficacy of a prescribed therapy may yield useful information. It should be noted that human carriers of *S. pneumoniae* who show no disease symptoms often do not have sufficient pathogen present to have *S. pneumoniae* antigens present in their urine.

A very recent article describes the successful diagnosis of meningitis caused by *S. pneumoniae* using an EIA method to test samples of cerebrospinal fluid. In the EIA, a monoclonal immunoglobulin A antiphosphoryl-choline antibody was employed to detect the C-polysaccharide antigen. See Stuertz, K, Merx, I, Eiffert, H., Schmutzhard, E., Mader, M. and Nau, R., 36 *J. Clin. Microbiol.* 2346-2348. The results obtained compared favorably with those reported by Yolken, R. H., Davis, D., Winkelstein, J., Russell, H. and Sippel, J. E., 20 *J. Clin. Microbiol.* 802-805 (1984) obtained in an EIA in which two antibodies for *S. pneumoniae* in cerebrospinal fluid were used—a horse antibody to the pneumococcal C-polysaccharide antigen, bound to microtiter plates, and a pooled rabbit antiserum to the polysaccharide capsular antigen in the liquid phase.

BRIEF DESCRIPTION OF THE INVENTION

According to the present invention, antibodies to the C-polysaccharide antigen of *S. pneumoniae* raised in rabbits are affinity purified with isolated and purified C-polysaccharide antigen having less than about 10% protein content.

These affinity purified antibodies are conjugated to an agent which produces a color reaction upon the formation of a sandwich with *S. pneumoniae* C-polysaccharide antigen from a test sample and additional affinity purified C-polysaccharide antibody immobilized upon a nitrocellulose matrix.

The test is conducted in a disposable immunochromatographic test device and requires no instrumentation to interpret the result. It can easily and successfully be performed by persons who have no training in laboratory techniques.

The preferred test sample for diagnosis of *S. pneumoniae*-caused pneumonia is patient urine, but the test also works with other bodily fluid samples that contain *S. pneumoniae*, including serum and sputum. Diagnosis of *S. pneumoniae*-caused meningitis may be readily made using patient cerebrospinal fluid as the test sample.

This invention for the first time offers the benefit of a test for *S. pneumoniae* that is performable within a 15-minute time span and is of at least equal specificity and sensitivity to EIA tests requiring eight to twelve times as long and much more work, to obtain a result. The test is easy to perform, requires no special training, equipment, or instrumentation and it enables a rapid diagnosis of pneumonia caused by *S. pneumoniae*. It can be readily performed in a doctor's office, thus permitting the patient to be immediately placed on a *S. pneumoniae*-specific therapeutic regimen. It can, of course, be performed in a clinical laboratory, but it can also easily be performed in a geriatric center, in a patient's home or in any environment where *S. pneumoniae*-caused pneumonia or other pathogenic condition is suspected to be epidemic.

The test of this invention is important to administer when disease states such as otitis media, bronchitis or sinusitis appear because once it can be established that any of these is due to *S. pneumoniae* rather than another infectious agent, appropriate therapy can promptly be initiated. Small children are especially prone to otitis media because of the shorter length and smaller diameter of their Eustachian tubes, so that early detection of *S. pneumoniae* if present may well forestall the onset of a more serious, or even life-threatening, disease state. Papers by Norris et al, *J. Pediatrics*, 821-827 (1966) and Hongeng et al, 130 *J. Pediatrics*, No. 5 (May 1997) indicate that children with sickle cell disease are highly susceptible to *S. pneumoniae* infection, with *S. pneumoniae* sepsis being the most common invasive infection among this populace and those once so infected having a much heightened risk of recurrence and subsequent death. Clearly, employing the ICT test of this invention to test the urine of these patients on a regular basis may be helpful in diminishing the need for the unremitting penicillin prophylaxis that the second of these papers recommends.

The ease of performance of the test and its ability to detect the C-polysaccharide antigen of *S. pneumoniae* in urine suggests that this test should prudently be performed on patients without overt clinical signs of related infection who report feeling substantially under par. Any such patient in whom it is established that *S. pneumoniae* is present in significant enough quantities to give a positive urine ICT test is a predictable candidate for developing a more severe infection—and the ability to forestall the disease development before it becomes severe by administering appropriate therapy is newly presented by this invention.

As a part of developing the rapid test of this invention, applicants have also developed a novel purified form of the C-polysaccharide cell wall antigen that is indigenous to all serotypes of *S. pneumoniae*. This novel purified antigen is of special use in affinity purifying polyvalent antibodies raised in an animal against *S. pneumoniae* bacteria or against the crude C-polysaccheride antigen.

DETAILED DESCRIPTION OF THE INVENTION

Figure 1:
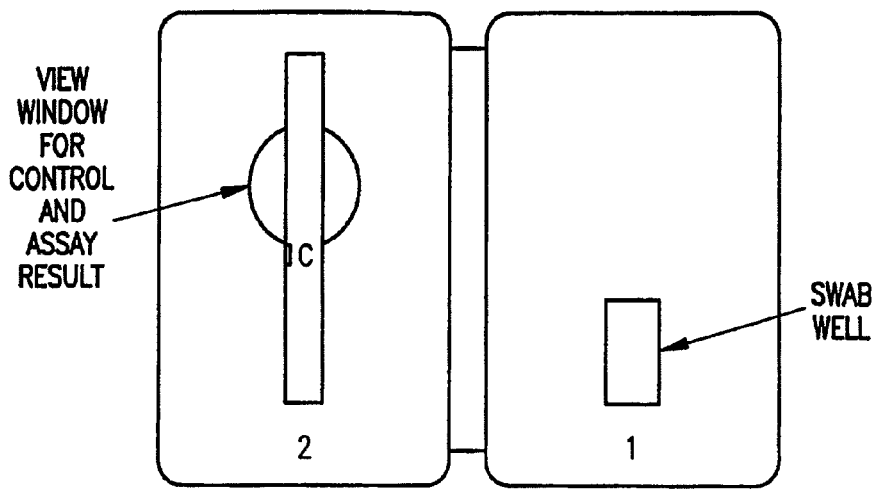
FIG. 1 and related FIGS. 1A, 1B and 1C hereof show the structure of a typical ICT device which has been adapted to perform the *S. pneumoniae* assay as hereinafter described in detail.

Broadly speaking, the ICT assay for *S. pneumoniae* as herein described may be designed and configured to be run on any known disposable ICT device disclosed in the art.

Preferably it is designed to be conducted, and is conducted, using an ICT device of the type disclosed in copending U.S. Patent Application Serial No. now U.S. Pat. No. 6,168,956 Ser. No. 07/706,639, of Howard Chandler, or one of its continuation-in-part applications, all of which are assigned to Smith-Kline Diagnostics, Inc. but are exclusively licensed to Binax, Inc. (which is entitled to assignment of this application), in a wide area of use fields that includes diagnoses of human respiratory system diseases.

The preferred device is suitably impregnated in one region thereof with antigen-specific polyvalent antibodies to the C-polysaccharide antigen of S. pneumoniae. Labeled antigen-specific antibodies are applied to another area of the device. The test sample suspected of containing S. pneumoniae is contacted first with the labeled antigen-specific antibodies, which then flow with the sample to the device area containing unlabeled bound antigen-specific antibodies, whereupon if S. pneumoniae is present in the sample, the labeled antibody: C-polysaccharide antigen conjugate already formed by contact binds to the immobilized unlabeled affinity purified antibodies, whereupon a visible color reaction is produced. The label may be any substance known in the art to produce visible color upon the reaction of a labeled antibody:antigen complex with bound unlabeled antibodies. Such labels include various finely divided metallics, various organic molecules, and various molecular combinations such as enzyme combinations with another color-producing molecule. In this invention, colloidal gold particles constitute the preferred label.

It is of major importance in designing the test device, that the concentration of antibody present at each of the two sites of the test device where reaction occurs be sufficient to insure that antigen present in the test sample will be captured by the labelled antibodies as the test sample contacts them and that labelled antibody: antigen conjugate will be readily captured and held by the bound antibodies at the sample capture line. Experimental work undertaken in connection with this invention has shown that active antibody to the C-polysaccharide antigen of S. pneumoniae must be present at each site of a test device at which antigen: antibody reaction is to occur, in a concentration of between 7.7 nanograms/sq. mm. of surface area and 385 nanograms/sq. mm. of surface area. If antibody concentrations lower than 7.7 nanograms/sq. mm. are present at a site where reaction is intended to occur, false negative results are likely.

Various methods of affinity purification of antibodies to the C-polysaccharide antigen of S. pneumoniae, are known. The one hereinafter described is preferred in the present invention, but others may be substituted. It is noted, however, that the affinity-purified antibodies of this invention are to be sharply distinguished from the "affinity-purified antibody preparation" which is described by Sjogren and Holme, 102 J. Immunol. Methods 93-100 (1987). These authors describe obtaining a hot phenol-purified C-polysaccharide antigen of S. pneumoniae containing 17% protein and absorbing it on an ion exchange gel, DEAE—Sepharose CL6B. After 48 hours incubation this preparation was packed into columns at approximately neutral pH of 7.2. The binding efficiency of the antigen to the gel is said to be about 60%. Antibodies were passed over these columns and incubated for 30 minutes, followed by elution of the columns with 0.5 M NaCl in PBS. It is known that leakage of antigen from ion-exchange columns is a frequent occurrence. In this system, it is reasonable to hypothesize that the product eluted from the gel was an in situ-formed immune complex of antibodies and antigen rather than a preparation of the purified antigen of this invention. It should particularly be noted that, in this invention, the purified antigen containing less than 10% protein is covalently coupled to a spacer molecule such as BSA—hydrazine conjugate, and the resulting labile antigen-conjugate ligand is then covalently coupled to a chromatographic gel—e.g., the Formyl Spherilose of Example 4, which is then applied to a column. The antibodies are added and eluted, with strongly acidic buffer, from the immobilized antigen on the column.

The antibody herein preferred is raised by conventionally injecting a rabbit with S. pneumoniae strain R6, a non-encapsulated S. pneumoniae strain available from the American Type Culture Collection under ATCC No. 39938 which is subjected to heat-killing of the cells before injection into the animal. After an appropriate time period, the animal is bled to obtain serum containing the desired antibodies, followed by purification thereof. Other antibodies to the S. pneumoniae C-polysaccharide antigen may be substituted for those specifically described herein without departing from this invention.

The antibody should initially be tested for cross reactivity to other common infectious bacteria. The preferred antibody referred to herein was tested, using the ELISA method, for cross-reactivity with each of the following: Citrobacter freundii, Staphylococcus aureus, Enterobacter cloacae, Enterobacter faecalis, Streptococcus Group B Type III, E. coli, Neisseria meningitidis, Salmonella cubana, Salmonella paratyphi A, Klebsiella pneumoniae, Streptococcus Group B type II, Staphylococcus epidermidis, Salmonella enteritidis, Streptococcus Group A, Serratia marcescens, Candida albicans, Haemophilus influenzae, Moraxella catarrhalis, Corynebacterium kutscheri, Pseudomonas putida, Proteus vulgaris, Enterococcus avium, Acinetobacter baumannii, Klebsiella oxytoca, Acinetobacter lwoffii, Pseudomonas aeroginosa, Staphylococcus saphrophyticus, Enterococcus durans, Corynebacterium bovis, Proteus mirabilis, Pseudomonas stutzeri, Pseudomonas cepacia, Salmonella typhi, Streptococcus Group F, Streptococcus Group B type 1a, Candida stellatoides, Streptococcus parasanguis, Streptococcus Group G, Streptococcus Group C, Streptococcus mutans, Morganella morganii, Staphylococcus haemolyticus, Haemophilus influenzae type B, Stenotrophomonas maltophilia, Haemophilus influenzae type D, Gardnerella vaginalis, Streptococcus mitis, Haemophilus parainfluenzae, Streptococcus sanguis, and H. influenzae nontypeable.

The only significant cross reactivity found was with Streptococcus mitis and Staphylococcus aureus. The first, S. mitis, is a causative agent for endocarditis, the overt patient symptoms of which physicians can readily distinguish clinically from those of an S. pneumoniae lung infection. S. mitis contains the same C-polysaccharide antigen as S. pneumoniae and the two share the ability to cause endocarditis, albeit S. pneumoniae normally does so in patients whose primary pneumonia has not been appropriately treated and who may then develop bacteremia and/or endocarditis or another pathogenic secondary infection. S. mitis, by contrast, is not a causative agent for pneumonia; endocarditis attributable to S. mitis normally develops independently of any other infection. It is accordingly believed that suspected cases of primary endocarditis caused by S. mitis can be confirmed, when needed, using the assay of this invention. It should be noted, however, that S. mitis is less likely to be present in urine than S. pneumoniae and hence, an assay of blood serum may be more likely to yield confirmatory information in that instance.

Some strains of S. aureus are known to secrete Protein A, a non-specific protein which indiscriminately binds IgG, and hence, all antibodies. The suspected presence of these S.

*aureus* entities may be readily confirmed or ruled out by running other simple tests well known in the art. (As shown in Example 9, *S. aureus* strains in which protein A is not present show no cross reactivity to the antibody of this invention.) A minor cross-reaction with *Haemophilus influenzae* was observed, but is not believed to be significant enough to cause a problem in the detection of *S. pneumoniae* in urine samples.

The following examples illustrate the preferred mode of affinity purification of the antibody, including the preliminary separation and purification of the antigen used to effect antibody purification, thus yielding an antigen-specific polyvalent antibody preparation.

EXAMPLE #1

Bacterial Growth Conditions

*S. pneumoniae* strain R6 (ATCC No. 39938) was grown in *S. pneumoniae* broth supplemented with 20 mM of Hepes buffer. The broth had the following composition per liter:

| | |
|---|---|
| Pancreatic digest of casein | 17.0 g. |
| Glucose | 10.0 g. |
| NaCl | 5.0 g. |
| Papain digest of soybean meal | 3.0 g. |
| Yeast extract | 3.0 g. |
| $K_2HPO_4$ | 2.5 g. |
| HEPES | 20 mM |

This broth had an initial pH of 7.2±0.2 at 26° C. It was autoclaved for 15 minutes at 15 psi and 121° C. and set aside to cool.

Frozen aliquots of *S. pneumoniae* strain R6 (ATCC No. 39938) were inoculated onto 5% sheep blood agar plates and allowed to grow. Growth from the plates was harvested in smaller aliquots of the seed broth and this seed broth was inoculated into three flasks, each containing 1,700 ml of supplemented *S. pneumoniae* broth of the composition shown above and further grown at 37° C. in an atmosphere of 5 percent $CO_2$, with agitation but not aeration. When the pH of the broth fell below 5.5 (its late log phase) the flasks were removed from the incubator, the cells were killed with 0.1 percent sodium azide and the pH was adjusted to above 7.0 to prevent autolysis. The flasks were then stored at 4° C. overnight. The following day, the suspension from each flask was centrifuged at 8,000 rpm for 60 minutes. The pellets were then combined and recentrifuged at 13,000 rpm for 30 minutes. The wet weight of the pellet was recorded and it was stored at −20° C.

EXAMPLE #2

Isolation of *S. Pneumoniae*

C-polysaccharide Antigen Containing Less than 10% Protein

Cells grown, treated and stored as in Example 1 were thawed at room temperature and suspended in phosphate-buffered saline solution ("PBS") of pH 7.2 with 0.2 percent of sodium azide in a ratio of 1.2 ml. of buffer to 1 gram of wet cells and left at room temperature for two days.

Eleven ml per gram of the wet cells of 0.1 N NaOH was then added to the *S. pneumoniae* suspension (in phosphate buffered saline), resulting in a pH of 12.34 (as measured by pH meter) and incubated for 45 minutes at about 30° C. The pH of the suspension was then adjusted to 2.75 (measured by pH meter) with 2 N HCl, followed by centrifuging the suspension at 3,500 rpm for 25 minutes. The supernatant was then separated and its pH was adjusted to 7.0-7.1 with 1 N NaOH. This essentially neutralized supernatant was dialyzed at 4° C. against water for two days in dialysis tubing (obtained from Spectra/Por) having a molecular weight cut-off of 12,000 to 14,000. The dialyzed supernatant was concentrated 25 to 40 times on a vacuum rotary evaporator.

Proteinase K (from Boehringer Mannheim) in the amount of 0.20 mg. per gram of wet cells, was added and the mixture was allowed to stand at 37° C. for three and one-half to four hours and then at room temperature overnight and the next day.

Following digestion with Proteinase K, the resulting supernatant was dialyzed at 4° C. against water in the dialysis tubing from Spectra/Por having a molecular weight cut-off of 12,000-14,000. The dialyzed supernatant was thereupon divided into 12 aliquots, each of which was placed in a 30 ml glass tube and mixed with an equal volume of 90 percent phenol. The tubes were closed and incubated for 23 minutes at 68-72° C. in a thermal water bath wherein the water level was slightly above that of the mixture level in the tubes. The suspension in each of the tubes was occasionally stirred with a glass Pasteur pipette to make the suspension more nearly homogeneous to the naked eye. After this incubation, the suspension was allowed to stand at room temperature for 30 minutes and then was centrifuged at 5,000 rpm for 40 minutes at a temperature of 15° C.

The upper water phase in each tube was then carefully withdrawn with a glass syringe; its volume was carefully measured for each individual tube and it was replaced with an equal volume of fresh water. The steps of incubation of the suspension at 68-72° C. followed by centrifugation at 5,000 rpm for 40 minutes at 15° C., was performed again and repeated then repeated once.

The lower phenol phase in each of the tubes was then carefully withdrawn with a glass syringe, leaving the intermediate (mixed water-phenol) and upper (water) phases in the tubes.

Meanwhile a flask containing cold ethanol, in a volume ratio of about 10:1 relative to the combined extracted phenol phase from the tubes, was placed in an ice bath. To this flask the phenol phase was slowly added, drop by drop, with intensive stirring. After all of the phenol phase was added, stirring was continued for 10 to 15 minutes, whereupon the mixture was placed in a refrigerator at 4° C. and left overnight to foster pelleting of the C-polysaccharide antigen. The following day the mixture was subjected to centrifugation at 12,000 rpm for 20 minutes at 4° C. The resulting pellet of C-polysaccharide antigen was suspended in about 0.4 ml per gram of wet cells of water and dialyzed against distilled water at 4° C. overnight, using the Spectra/Por tubing with molecular weight cut-off of 12,000-14,000 referred to above. The resulting aqueous solution of C-polysaccharide antigen was lyophilized and weighed. Its protein concentration was evaluated by the Lowry Method; its composition was checked on SDS-PAGE (12 percent gel) by Western immunoblot assay and its C-polysaccharide antigen activity was checked by ELISA.

This operation was repeated a number of times. It was found that the overall yield of *S. pneumoniae* C-polysaccharide antigen was from 1.2 to 1.4 percent per gram of wet cells of *S. pneumoniae* strain R6, while its protein content was between about 5 and about 8 percent.

It should be noted that, in general, C-polysaccharide antigen preparations with a protein content exceeding 10% are less likely to perform satisfactorily in this invention than preparations of less than 10% protein content.

EXAMPLE #3

Preparation of BSA Conjugate of the Antigen

For coupling of the purified *S. pneumoniae* strain R6 C-polysaccharide antigen to a chromatographic column to permit affinity purification of rabbit anti-*S. pneumoniae* strain R6 antibodies, a BSA-hydrazine conjugate was selected. Other known materials having similar functions may be selected and conjugated to accomplish this coupling function.

The BSA-hydrazine conjugate was prepared as follows:

Hydrazine dihydrochloride obtained from Aldrich Chemical Co. was dissolved in water to produce an 0.5 M solution. The pH was adjusted to 5.2 with dry NaOH and dry bovine serum albumin ("BSA") from Sigma Chemical Co. was added to produce a final concentration of BSA of 25 mg per ml of solution. After complete dissolution of BSA, N-(dimethylaminopropyl)-N'-ethylcarbodiimide hydrochloride (from Fluka Chemical Co.) was added in a quantity to produce a final concentration of 2.5 mg per ml of solution. This reaction mixture was incubated at room temperature, with continuous stirring, overnight. The next day, it was intensively dialyzed against distilled water at 4° C. Concentration of conjugate was measured (as BSA concentration) at 280 nm on a Beckman DU 640 spectrophotometer.

To couple this conjugate to *S. pneumoniae* strain R6 C-polysaccharide antigen, the procedure was as follows:

The dry preparation of the antigen was dissolved, in the amount of 1.1 mg per ml, in distilled water. Using diluted HCl, the solution pH was adjusted to 5.0-6.0. BSA:hydrazine conjugate in aqueous solution in a concentration of 23 mg per ml was treated with dilute HCl to bring its pH to between 4.0 and 5.0, and this solution was then slowly added to the antigen solution in a volume ratio of about 1:6.65 (about 3:1 by weight). After three minutes of stirring, N-(dimethylaminopropyl)-N$^1$-ethylcarbodiimide hydrochloride (from Fluka Chemical Co.) in about 100 to 200 mcl of distilled water was added to the reaction mixture in a N-ethylcarbodiimide hydrochloride to C-polysaccharide antigen weight ratio of about 1 to 1.92.

After stirring for two hours at room temperature, the pH of the resulting mixture was adjusted to about 9.0 with dilute NaOH. The incubation was thereupon continued at room temperature for one hour and then at 4° C. overnight.

EXAMPLE #4

Affinity Column Preparation and Antibody Purification

To the ligand solution from Example 3, dilute HCl was added to bring its pH to 7.0. Formyl Spherilose from Isco, Inc. was selected as the matrix for the immunoadsorbent gel. The ligand of C-polysaccharide antigen was coupled to this matrix using known procedures, e.g., as described in Spherilose applications, ISCO Applications Bulletin 78 at pages 28-35. Other known matrices and coupling procedures may be substituted.

The gel was packed into the column and washed alternatively with distilled water, 0.2 M glycine-HCL solution of pH 2.5, triple strength phosphate-buffered saline of pH 7.2 and regular strength PBS of pH 7.2, using 5 to 10 volumes per volume of the gel of each solution.

The resulting activated column was then used for affinity purification of antibodies, thus producing antigen-specific antibodies, as follows:

Rabbit antiserum to *S. pneumoniae* Strain R6 (ATCC No. 39938) directed to whole heat-killed cells, was mixed with dry NaCl to a final concentration of 0.5 M. This mixture was centrifuged at 8,500 rpm for 20 minutes and the supernatant was filtered through cotton wool. The filtrate was applied on the affinity column. The unbound components were washed from the column with triple strength phosphate buffered saline of pH 7.2 and with regular strength phosphate buffered saline of pH 7.2. The antibodies were eluted from the column with 0.2 M glycine-HCl buffer of pH 2.5. The eluent was monitored at 280 nm on the Beckman spectrophotometer and the fractions containing antibodies were pooled in a flask which was placed in an icewater bath. The pooled fractions were neutralized with aqueous 0.5 M $NaH_2PO_4$ of pH 9.0.

The concentration of antibodies was evaluated from the absorbance value at 280 nm on the spectrophotometer.

The antibody solution was dialyzed against PBS of pH 7.2 and concentrated on a PM-10 filter obtained from Amicon until a concentration of 0.8-1.5 mg/ml of antibody was achieved.

It was found that 18-20 mg of affinity purified antibodies were recovered from each 25 ml of rabbit antiserum to *S. pneumoniae* strain R6 so treated.

These affinity purified antibodies were utilized in an ICT test specific for *S. pneumoniae* C-polysaccharide antigen as described in the ensuing example.

EXAMPLE #5

ICT Device and its Preparation

Figure 1A:
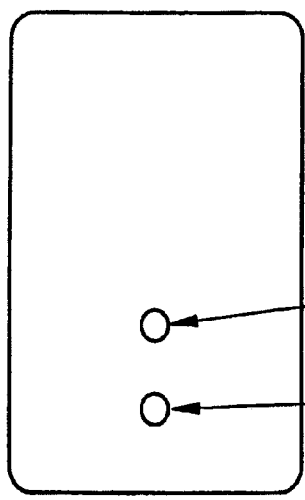

A. Preparation of Test Device:

A test device comprising a hinged cardboard housing equipped with a window to allow the viewing of both the test results and control results was prepared as shown in FIG. 1. The device has a recess into which is placed a preformed plastic swab well for receiving the sample-wetted swab on the right-hand (labeled 1 in the drawing). An overlabel shown in FIG. 1A is then placed over the entire right-hand side of the device. The overlabel has been equipped with two holes—a lower one (marked B on FIG. 1A) into which the saturated swab is to be inserted and an upper one (marked B on FIG. 1A) toward which the swab will be pushed after insertion thereof into the hole B. The position of the overlabel with its holes A and B, and the swab well cooperate to hold the swab in a proper position during the assay and to promote the expulsion of sorbed liquid from the swab.

Figure 1B:
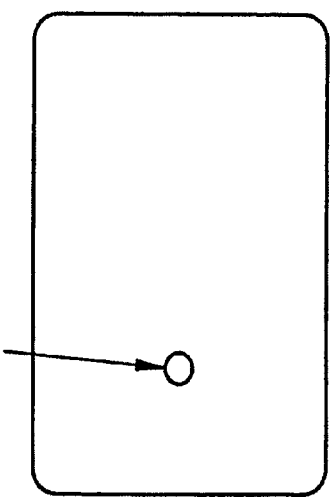

A preassembled test strip (marked C on FIG. 1) described below, is inserted into the recess (labeled 2 on FIG. 1) and held in place by an adhesive applied to the bottom thereof. An overlabel shown in FIG. 1B is placed atop the left-hand side. It has been equipped with a single hole (marked D in FIG. 1B) which mates to the right-hand side hole A when the device is closed for performance of the assay.

The assembled device is stored in a sealed pouch with desiccant until it is used. Prior to sealing the pouch and storing, a lightly adhesive tape is placed on the outer edge of the right-hand half of the device.

Figure 1C:
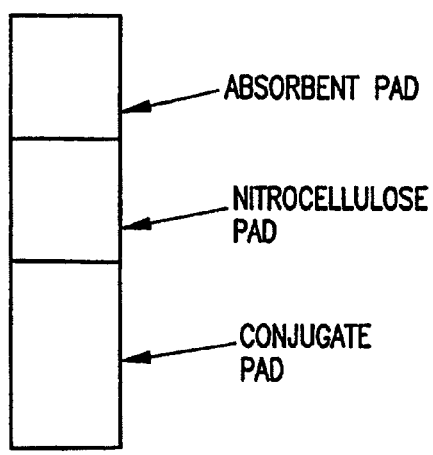

B. Construction and Preparation of the Test Strip:

FIG. 1C shows the construction of the preassembled strip. It is comprised of a conjugate pad of sorbent material in which a conjugate of gold particles and the antigen-specific rabbit anti-*S. pneumoniae* C-polysaccharide antigen antibodies described above have been impregnated. A bridge pad of Ahlstrom 1281 (not shown) connects the conjugate pad to a nitrocellulose pad onto which a capture line for the sample which reacts with the conjugate has been established by embedding a stripe of antigen-specific rabbit anti-*S. pneumoniae* C-polysaccharide antigen antibodies, prepared as described above. The nitrocellulose pad also has a downstream control line established by striping the pad with goat anti-rabbit immunoglobulin (IgG). Following the nitrocellulose pad, the strip is ended by an absorbent pad which serves as a reservoir for liquid. All of these pads are backed by an adhesive strip and placed into a device.

The conjugate pad is normally made from non-woven polyester or extruded cellulose acetate. To prepare this pad for use in the assay, gold particles of 50 nm. diameter are conjugated to affinity-purified rabbit anti-*S. pneumoniae* C-polysaccharide antibodies prepared as described above. The conjugation is effected using a known method such as that described by DeMay in Polak, J. M. and Van Norden, S. (Eds.), *Immunochemistry: Modern Methods and Application*, (Wright, Bristol, England, 1986). The gold conjugate particles are mixed with a drying agent consisting of aqueous 5 mM sodium tetraborate of pH 8.0 containing 1.0 percent BSA, 0.1 percent Triton X-100, 2.0 percent Tween 20, 6.0 percent sucrose and 0.02 percent sodium azide. The pad is heated sufficiently to remove all of the liquid present and stored in a low-humidity environment pending assembly of the test strip. These pads and their treatment are especially chosen so that the pads will hold the dry conjugate and will release it only when later wetted by sample.

The nitrocellulose pad is first treated by embedding a stripe of affinity purified rabbit anti-*S. pneumoniae* C-polysaccharide antibodies in a first portion thereof, using a carrier solution of phosphate buffered saline. These antibodies act as the capture line. In a second portion of the pad downstream of the first one in the assembled test device, the control line is established by striping goat anti-rabbit IgG in the same carrier solution on the surface of the pad. The nitrocellulose pad is then subjected to desiccation at 18-25° C. to promote permanent absorption of the protein stripes thereto.

The absorbent pad used is of a commercially available cellulosic material sold under the name Ahlstrom 939. This pad requires no special treatment.

C. Kit Preparation:

As sold in commerce, the test device containing the finished test strip is assembled. In practice, a number of devices are packaged with a commensurate number of swabs fashioned from fibrous Dacron and a bottle of "Reagent A" equipped with a top adapted to deliver Reagent A dropwise. "Reagent A" is a solution of 2.0 percent Tween 20, 0.05 percent sodium azide and 0.5 percent sodium dodecyl sulfate in a 0.05 M sodium citrate-sodium phosphate buffer of pH 6.5. Positive and negative controls are also included in each kit.

EXAMPLE #6

Conducting the ICT Assay

In practice, the swab furnished with each device is dipped into the liquid sample, completely immersing the swab head. The use of the swab to act as a filter for undissolved solids, semisolids and colloids present in liquid biological samples such as urine, blood, lymph, etc., and also in liquid environmental samples is the subject of copending, commonly assigned, application Ser. No. 09/044,677, now U.S. Pat. No. 6,548,309, of Norman Moore and Vincent Sy filed Mar. 19, 1998, which is assigned to Binax, Inc. The swab is inserted into the hole at the bottom of the device (hole B of FIG. 1A) and gently pushed upward so that the swab tip is visible in the top hole (hole A of FIG. 1A). The Reagent A vial is held vertically above hole B and three drops of Reagent A are slowly added. The adhesive liner is then immediately peeled from the right edge of the device and the device is closed and securely sealed, thus pressing the swab in the swab well against the gold conjugate pad. After 15 minutes, the result can be read in the window of the device. A negative sample—i.e., one not containing identifiable *S. pneumoniae* C-polysaccharide antigen—will exhibit only the control line in the top half of the window. A positive sample containing the target antigen will show two lines, the lower one of which is the patient (or sample) line; even a faint sample line indicates the presence of the target antigen in the sample. If no line appears in the window after 15 minutes, or only a sample line appears in the lower part of the window, the test is invalid and must be repeated.

Using the procedure described above, the devices prepared as described in Example 5 were tested using the ICT procedure just described against 146 patient urine samples obtained from Centers for Disease Control. Since the patient diagnoses relative to the presence of *S. pneumoniae* infection were based on a variety of different indications including blood culture, Gram stain, sputum culture, Autolysin PCR and Pneumolysin PCR, but urine assay results had not been made, each of these samples was tested in our laboratory with ICT as herein described and also with ELISA, for the presence of *S. pneumoniae* C-polysaccharide antigen.

Personnel performing the ICT and ELISA assays were not apprised of the Centers for Disease Control classifications of the urine samples as having been collected from patients diagnosed as positive or negative for *S. pneumoniae* infection. It was found that the ICT and ELISA results were, at the very least, comparable in terms of both sensitivity and specificity in some 134 instances. It is noted, however, that in some instances neither the ELISA nor the ICT tests could be fully correlated to the patient diagnoses supplied by Centers for Disease Control. It is believed that the art-recognized inadequacies of culture evaluation as a basis for diagnosis of *S. pneumoniae* infection and the fact that no information was available concerning either the therapy administered to any of the patients, or the time therapy was commenced relative to the time the urine sample was collected are factors that preclude any completely meaningful comparison of all the results.

The substantial comparability of ICT and ELISA results in 134 instances confirms the considerable advantages that the 15-minute ICT test of this invention offers in terms of rapid diagnosis of *S. pneumoniae*-caused infection and consequent early institution of the most effective patient therapy.

EXAMPLE #7

Clinical Trials

Using the devices prepared as described in Example 5 and the ICT procedure as described in Example 6, first paragraph, clinical studies were conducted at three sites, using a bank of characterized specimens. These included 273 urine specimens collected from hospitalized patients and outpatients. Among the 273 patients, 35 gave positive blood culture results and 238 gave negative blood culture results. (It should be noted that culture methods often vary substantially from place to place. The urine samples of the blood culture positive patients were presumed to have been collected within 24 hours of both blood collection and initial administration of antibiotics. Of the 238 urine samples from patients with blood that tested negative in blood culture tests, 28 were collected from bacteremic patients, 4 from patients with empyema, 53 from patients with pneumonia and 153 from patients with urinary tract infections).

In addition, 100 urine samples, which were collected from individuals with no known infection, were assayed in the test of this invention, involving the devices prepared as in Example 5 and the ICT procedure described in Example 6. Blood samples from these individuals gave negative results in culture tests.

Of the 35 urines from patients testing positive for *S. pneumoniae* in blood culture tests, 30 gave positive results in the test of this invention and 5 gave negative results. Of the 338 urine samples from patients, all of whom tested negative in blood culture tests and 100 of whom were presumed negative, 21 tested positive in the ICT test of this invention and 317 tested negative. The sensitivity of the ICT test was calculated as 86%, the specificity as 94% and the accuracy as 93%.

It should be noted that of the patients whose urine tested positive for *S. pneumoniae* by ICT and whose blood cultures gave negative results for *S. pneumoniae*, it was established by other tests that of those with urinary tract infections 5 had *E. coli* infections, 2 had *Enterobacter cloacae* infections, 3 had *lactobacillus* infections, 1 was infected with *Providencia Stuartii*, 1 with *Staphylococcus aureus*, 1 with *Streptococcus* (non A, nonB) and 1 with a *Streptococcus* (nonD) infection. Two of those who had pneumonia also were infected with *Mycobacterium tuberculosis* and one with *Mycobacterium kansasii*. One bacteremic patient was infected also with *Proteus mirabilis*. Four patients with no known infection had urine samples that tested positive with the ICT test of this invention.

EXAMPLE #8

Clinical Trials

Tests were conducted at seven hospitals, six in the United States and one in Spain to evaluate 215 urine specimens from both hospitalized and outpatients with at least one of lower respiratory symptoms and sepsis symptoms or who were otherwise suspected of harboring pneumococcal pneumonia. In these tests, the device prepared in accordance with Example 5 was utilized in the procedure of Example 6 and the results were compared with blood culture results conducted on blood specimens from the same patients. No effort was made to assure uniformity of culture methods among the participating institutions.

The blood culture results yielded 31 positive assessments for *S. pneumoniae* and 184 negative assessments. Of the 31 patients whose blood culture results were positive, the ICT test of this invention conducted on urine samples showed 28 positives and 3 negatives. Of the 184 patients whose blood culture results were as assessed negative, 45 provided urine samples that tested positive in the ICT test of this invention while 139 urine samples from these patients tested negative. Sensitivity in this trial for the test of the invention was calculated as 90%, specificity as 76% and accuracy as 78%.

The results obtained with the ICT tests of this invention in Examples 7 and 8 must be considered in the light of the well-known problems associated with culture tests and the known likelihood that about 80% of patients infected with pneumococcal pneumonia will not produce blood specimens that contain *S. pneumoniae*. It is believed that further experience with the assay of this invention will demonstrate convincingly that its specificity, sensitivity and accuracy are understated in Examples 7 and 8 due to the use of blood culture tests for comparison purposes.

EXAMPLE #9

Further Cross-Reactivity Testing

Using the device prepared as in Example 5 and the procedure of Example 6, some 144 organisms at concentrations of $10^6$ to $10^9$ CFU/mL were tested. Each of the organisms tested was grown on appropriate agar and incubated at 37° C. in 5% $CO_2$ overnight, whereupon the plates were checked for purity and well isolated colonies of each organism were selected for testing.

Of the 144 organisms, only one—*S. mitis*—A.T.C.C. #49456, gave a positive test and hence was cross-reactive. This was expected, as noted above, because *S. mitis* is known to contain the C-polysaccharide cell wall antigen which the test of this invention is designed to detect.

Negative results in the assay of the invention were obtained with each of the following: *Acinetobacter anitratus* (ATCC #49139) *Acinetobacter baumanii* (ATCC #1906-T), *Acinetobacter calcoaceticus* (ATCC No. 49466), *Acinetobacter haemolyticus* (A.T.C.C. #19002), Adenovirus 2 and 3 (pooled pure culture sample obtained from Center for Disease Control), *Alcaligenes faecalis* (A.T.C.C. #6633), *Bordetella pertussis* (A.T.C.C. #3467), *Branhamella catarrhalis* (A.T.C.C. #25238-T), *Blastomyces dermatitidis* (pure culture obtained from Center for Disease Control, strain number unknown), *Candida albicans* (A.T.C.C. #'s e10231, 14053 and 60193, each tested separately), *Candida stellatoides* (A.T.C.C. #11006), *Citrobacter freundii* (A.T.C.C. #375GT), *Coccidiodes immitis* (pure culture from Center for Disease Control, strain number unknown), *Corynebacterium kutscheri* (A.T.C.C. #15677-T), *Corynebacterium matruchotii* (A.T.C.C. #14266-T), *Corynebacterium pseudodiphteriticum* (A.T.C.C. #10700-T), *Enterobacter cloacae* (A.T.C.C. #'s 13047-T, 23355, 35030 and 49141, each tested separately), *Enterococcus avium* (A.T.C.C. No. 49462), *Enterococcus durans* (A.T.C.C. #49135), *Enterococcus faecalis* (A.T.C.C. #'s 19433-T, 29212, 49477, 49478, 49149 and 51299, each tested separately), *Escherichia coli* (A.T.C.C. #'s 23513, 8739, 23514, 25922, 35218, 1173GT, 35421 and 15669 and one unnumbered sample, each tested separately), *Escherichia hermannii* (A.T.C.C. 33650-T and 4648GT, each tested separately), *Flavobacterium indologenes* (A.T.C.C. #49471), *Flavobacterium meningosepticum* (A.T.C.C. #49470), *Gardnerella vaginalis* (A.T.C.C. #14018-T), *Haemophilus influenzae*, a (A.T.C.C. #9006), *Haemophilus influenzae*, b (A.T.C.C. #'s 9795 and 33533, each tested separately), *Haemophilus influenzae*, c (A.T.C.C. #9007), *Haemophilus influenzae*, d (A.T.C.C. #9008), *Haemophilus influenzae*, e (A.T.C.C. #8142), *Haemophilus influenzae*, f (A.T.C.C. #9833, *Haemophilus influenzae*, NT (A.T.C.C. #'s 49144, 49247 and 49766, each tested separately), *Haemophilus parainfluenzae* (A.T.C.C. #3339Z-T, obtained as a pure culture from Center for Disease Control), *Histoplasma capulatum* (Two separate pure cultures from Center for Disease Control, strains unknown, each tested separately), *Klebsiella oxytoca* (A.T.C.C. #'s 43086 and 49131, each tested separately), Klebsiella pneumoniae (A.T.C.C. #'s 13882, 13883-T and 49472, each tested separately), Lactobacillus acidophilus (A.T.C.C. #4356), Lactobacillus casei (A.T.C.C. #393), Lactobacillus gasseri (A.T.C.C. #33323), Lactobacillus jensenii (A.T.C.C. #25258), Legionella pneumophila (A.T.C.C. #33152), Listeria monocytogenes (A.T.C.C. #7644), Micrococcus luteus (A.T.C.C. #'s 9341 and 49732, each tested separately), Moraxella osloensis (A.T.C.C. #15276), Morganella morganii (A.T.C.C. #25830-T), Mycoplasma genitalium (A.T.C.C. #33530, obtained as a pure culture from Center for Disease Control), Mycoplasma hominis (A.T.C.C. #27545, obtained as a pure culture from Center for Disease Control), Mycoplasma pneumoniae (FH Type 2, obtained as a pure culture from Center for Disease Control), Neisseria cinerea (A.T.C.C. #14685), Neisseria gonorrheae (A.T.C.C. #'s 8660, 19424-T and 27631, each tested separately), Neisseria lactamica (A.T.C.C. #23970-T), Neisseria meningitidis (A.T.C.C. #13077-T), Neisseria subflava (A.T.C.C. #49275), Nocardia farcinia (obtained as a pure culture from Center for Disease Control), Paracoccidiodes brasiliensis (strain # unknown, obtained as a pure culture from Center for Disease Control), Parainfluenzae Type 1 (strain C 39, obtained as a pure culture from Center for Disease Control), Parainfluenzae Type 2 (strain H A 47885, obtained from Center for Disease Control as a pure culture), Proteus mirabilis (A.T.C.C. #'s 7002 and 12453, each tested separately), Proteus vulgaris (A.T.C.C. #'s 13315-T and 49132, each tested separately), Providencia stuartii (A.T.C.C. #49809), Pseudomonas aeruginosa (A.T.C.C. #'s 15442 and 27853, each tested separately), Pseudomonas cepacia (A.T.C.C. #25416-T), Pseudomonas pickettii (A.T.C.C. #49129), Pseudomonas putida (A.T.C.C. #49128), Pseudomonas putrefaciens (A.T.C.C. #49138), Pseudomonas stutzeri (A.T.C.C. #17588-T), Respiratory Syncitial Virus, pooled (Pooled sample of Strain A2 and A.T.C.C. #18573, each obtained from Center for Disease Control as a pure culture), Rhinovirus (A.T.C.C. #'s 088 and 077, each obtained as a pure culture from Center for Disease Control and each tested separately), Salmonella cubana (A.T.C.C. #12007), Salmonella enteritidis (A.T.C.C. #13076-T), Salmonella paratyphi A (A.T.C.C. #9150), Salmonella typhi (A.T.C.C. #6539), Serratia marcescens (A.T.C.C. #13880-T), Sphingobacterium multivorum (A.T.C.C. #35656), Staphylococcus aureus (A.T.C.C. #'s 12598, 6538P, 25923, 29213, 43300 and 49476, each tested separately), Staphylococcus epidermidis (A.T.C.C. #'s 12228, 14990-T, 49134, and 49461, each tested separately), Staphylococcus haemolyticus (A.T.C.C. #29970-T), Staphylococcus saprophyticus (A.T.C.C. 15305-T and 49907, each tested separately), Staphylococcus xylosis (A.T.C.C. #49148), Stenotrophomonas maltophilia (A.T.C.C. #13637-T), Streptococcus anginosus (A.T.C.C. #9895), Streptococcus bovis (A.T.C.C. #49133), Streptococcus Group A (A.T.C.C. #'s 1357, and 19615, each tested separately), Streptococcus Group B (A.T.C.C. #'s 13813-T, 12386, 12400, 12401, 27591, 12973, 12403, and 31475, each tested separately), Streptococcus Group C (A.T.C.C. #12388), Streptococcus Group F (A.T.C.C. #12392), Streptococcus Group G (A.T.C.C. #12394), Streptococcus mutans (Shockman strain), Streptococcus parasanguis (A.T.C.C. #15909), Streptococcus sanguis (A.T.C.C. #10556-T), Trichomonas vaginalis (A.T.C.C. 085 and 520, each obtained as a pure culture from Center for Disease Control and tested separately).

EXAMPLE #10

Clinical Trial with Healthy and Sick Children

An as yet unfinished clinical trial with healthy and sick children as participants is in progress. Preliminary spot results show that, using devices prepared as described in Example 5 and following the procedure described in Example 6, S. pneumoniae was detected in urine of 2 of 3 children diagnosed with sinusitis. It is believed that the sinusitis case wherein the child's urine tested negative may involve a different causative agent.

In the same trials, S. pneumoniae was detected with the device and method of this invention in the cerebrospinal fluid of the only child who exhibited overt signs of meningitis, enabling prompt and effective therapeutic treatment of this individual.

EXAMPLE #11

Detection of S. Pneumoniae Antigen in Urine of Meningitis Patients

Two patients exhibiting overt clinical symptoms of meningitis were hospitalized. One had received antimicrobial therapy prior to admission; the other had not. From each, cerebrospinal fluid was obtained and subjected to a culture test. The test results were negative, and so were blood culture results.

As a last diagnostic resort, devices prepared according to Example 6 were utilized in the procedure described in Example 7 on urine samples obtained from each patient. In each case, the urine samples tested positive for the S. pneumoniae C-polysaccharide cell wall antigen.

These preliminary results strongly suggest that urine samples may be routinely utilized in lieu of cerebrospinal fluid to test for S. pneumoniae-caused meningitis. The ability to substitute urine for cerebrospinal fluid as a test medium, if confirmed by further clinical experience, will be of great benefit to patients and medical practitioners alike. Spinal taps, by which cerebrospinal fluid must be obtained, are painful for patients and somewhat hazardous as well. For medical practitioners, spinal taps are time consuming and require concentrated attention to detail.

Those skilled in the art of immunochemistry generally, and especially those skilled in immunoassays, will recognize that other materials and ingredients and at times, other procedural steps, can readily be substituted for those specifically recommended herein. A vast array of literature, both patent and non-patent, discusses the design and use of reliable, one-time-use, disposable immunoassay test devices that could be substituted for the preferred ICT device described and recommended herein. It is not intended that the present invention should be limited with respect to substitutable assay devices, materials, ingredients or process steps except insofar as the following claims may so limit it.

What is claimed is:

1. A device for determining the presence of Streptococcus pneumoniae in a liquid sample, the device comprising:

a porous test strip comprising a sample receiving zone;
multiple binding agents, each binding agent comprising:
    antigen specific polyclonal antibodies conjugated to a detectable particle, which specifically bind to a cell wall C-polysaccharide antigen of *Streptococcus pneumoniae* preparation,
multiple capture agents and
a capture zone;
wherein the porous test strip defines a liquid flow path extending downstream from the sample receiving zone and along which liquid received by the sample receiving zone can pass at least to the capture zone, the binding agents are disposed in a dried state along the flow path of the test strip downstream from the sample receiving zone and upstream from the capture zone, the binding agents are mobilizable by liquid passing along the flow path, and the capture agents are disposed in the capture zone and are each capable, in the presence of *Streptococcus pneumoniae* in a liquid sample received by the sample receiving zone, of binding a complex comprising one of the binding agents bound to the antigen.

2. The device of claim 1, wherein the capture agents are antibodies.

3. The device of claim 2, wherein the capture agents are polyclonal antibodies.

4. The device of claim 1, wherein the detectable particle is a color-producing particle.

5. The device of claim 4, wherein the detectable particle is colloidal gold.

6. The device of claim 1, wherein the detectable particle is a color-producing particle and the capture agents are antibodies.

7. The device of claim 1, wherein the presence of *Streptococcus pneumonia* in a liquid sample is determined within fifteen minutes of applying the liquid sample to the device.

8. The device of claim 1, wherein the antigen specific polyclonal antibodies specifically bind to a cell wall C-polysaccharide antigen indigenous to all serotypes of *Streptococcus pneumoniae*.

9. The device of claim 1, wherein the liquid sample is urine, serum, sputum or cerebrospinal fluid.

10. The device of claim 1, wherein the antigen specific polyclonal antibodies are affinity-purified.

11. The device of claim 10, wherein the antigen-specific polyclonal antibodies are affinity-purified with isolated and purified C-polysaccharide antigen of *Streptococcus pneumoniae*.

12. The device of claim 1, wherein the antigen-specific polyclonal antibodies specifically bind to a preparation of *S. pneumoniae* cell wall C-polysaccharide antigen that has not more than about 10% by weight of protein.

* * * * *